United States Patent [19]

Herzog et al.

[11] Patent Number: 4,957,100
[45] Date of Patent: Sep. 18, 1990

[54] ULTRASOUND GENERATOR AND EMITTER

[75] Inventors: Ludwig Herzog; Volker Knapp, both of Waldmichelbach, Fed. Rep. of Germany

[73] Assignee: Siemens Aktiengesellschaft, Berlin and Munich, Fed. Rep. of Germany

[21] Appl. No.: 165,548

[22] Filed: Mar. 8, 1988

[30] Foreign Application Priority Data

Mar. 20, 1987 [DE] Fed. Rep. of Germany ....... 3709110

[51] Int. Cl.⁵ .......................................... A61B 23/02
[52] U.S. Cl. .................................. 128/24 A; 310/317
[58] Field of Search ................... 128/24 A, 660.01; 310/334, 317; 361/397

[56] References Cited

U.S. PATENT DOCUMENTS

| | | |
|---|---|---|
| 2,565,159 | 8/1951 | Williams .............................. 310/335 |
| 3,727,112 | 4/1973 | Popescu . |
| 3,736,523 | 5/1973 | Puskus . |
| 4,181,864 | 1/1980 | Etzold . |
| 4,525,790 | 6/1985 | Nakamura . |
| 4,582,066 | 4/1986 | Barnes et al. .................. 128/662.03 |
| 4,587,958 | 5/1986 | Noguchi et al. ................. 128/24 A |
| 4,700,100 | 10/1987 | Congdon et al. .................... 310/316 |
| 4,791,915 | 12/1988 | Barsotti et al. .................... 128/24 A |
| 4,811,740 | 3/1989 | Ikeda et al. ..................... 128/660.01 |
| 4,819,652 | 4/1989 | Micco .............. 128/661.09 |

FOREIGN PATENT DOCUMENTS

| | | | |
|---|---|---|---|
| 0176136 | 4/1986 | European Pat. Off. . | |
| 8604208 | 7/1986 | PCT Int'l Appl. ................. | 361/397 |
| 2181302 | 4/1987 | United Kingdom ................ | 361/397 |

*Primary Examiner*—Ruth S. Smith
*Assistant Examiner*—John D. Zele
*Attorney, Agent, or Firm*—Hill, Van Santen, Steadman & Simpson

[57] ABSTRACT

An ultrasound generator and emitter suitable for use in ultrasound therapy has an electrical signal generator for charging an ultrasound resonator in an ultrasound head with electrical signals, which are converted into ultrasound energy to be emitted. The ultrasound head also includes an adapter element which electrically matches the particular ultrasound head being used to the electrical signal generator. The adapter is in the form of a removable adapter element which is electrically matched to the ultrasound resonator. The adapter element can be easily plugged into and removed from a circuit board in the ultrasound head. When the ultrasound resonator is replaced, the adapter element can be easily interchanged with an adapter element for matching the new ultrasound resonator to the signal generator.

6 Claims, 2 Drawing Sheets

ULTRASOUND GENERATOR AND EMITTER

BACKGROUND OF THE INVENTION

1. Field of the Invention

The present invention is directed to a device for generating and emitting ultrasound energy having an electrical signal generator and an ultrasound resonator contained in an ultrasound head, and means for electrically adapting the particular ultrasound head in use to the electrical signal generator. The ultrasound head is suitable for combined ultrasound and stimulation current therapy.

2. Related Application

The subject matter of the present application is related to the subject matter of an application entitled "Ultrasound Head With Removable Resonator Assembly," Helmreich et al, Ser. No. 165,549, filed simutaneously herewith.

DESCRIPTION OF THE PRIOR ART

An ultrasound generating and emitting device is described in European Application No. 0 176 136 wherein the ultrasound head has a resistance potentiometer which permits the particular ultrasound head in use to be matched to the electrical oscillation generator, by adjustment of the variable contact. A similar device is also known from the brochure "Impulsaphon-U, Dr. Born GmbH, Ultraschall-Therapiegeraet M100," 1983. An ultrasound head having an ultrasound resonator for ultrasound therapy is also described in German Application No. 33 24 575, however, this ultrasound head does not include a matching element.

In known devices of the type described above wherein matching is undertaken by resistance potentiometers, the matching or adaptation is usually undertaken at the site of manufacture, i.e., at the factory. Undertaking the matching directly at the place of use, for example in a clinic or in a physician's office is difficult because of the technical outlay required.

SUMMARY OF THE INVENTION

It is an object of the present invention to provide an ultrasound generating and emitting device having a matching element for matching the electrical signal generator to the particular ultrasound head being used wherein such matching can be undertaken directly at the place of use, for example, by a service technician.

It is a further object of the present invention to provide such an ultrasound generating and emitting device wherein such matching can be undertaken quickly and without significant technical outlay.

The above objects are achieved in accordance with the principles of the present invention in an ultrasound emitting and generating device having an ultrasound head containing an ultrasound transducer, and a remote driver circuit for the ultrasound transducer wherein the ultrasound head has a circuit board with an adapter element which can be easily plugged into, and removed from, the circuit board. The adapter element is in the form of a circuit on an IC base and is connected in the electrical signal path between the signal generator (driver) circuit and the ultrasound transducer. The ultrasound resonator in the ultrasound head is also removable, and each ultrasound resonator has an adaption element associated therewith, which electrically matches the ultrasound resonator to the signal generator. The components of the adaptation element are pre-set so that the particular ultrasound transducer in use in the ultrasound head is electrically matched to the driver circuit. As used herein, "preset" means that the necessary electrical adjustment of components of the adaptation element is undertaken prior to the actual installation of the adjustment element in the ultrasound head, so that further adjustment at the time and place of actual installation is not needed. When an ultrasound resonator is replaced, the adaptation element associated with the old resonator is removed, and a new adaptation element associated with the new ultrasound resonator is inserted in its place. The ultrasound resonator and the adaptation circuit are therefore always inserted in the same operation in the ultrasound head as a matched pair. By simply substituting a new pair in place of an old pair, the ultrasound head is automatically adapted to the electrical oscillation generator at the place of use.

DESCRIPTION OF THE PREFERRED EMBODIMENTS

Figure 1:
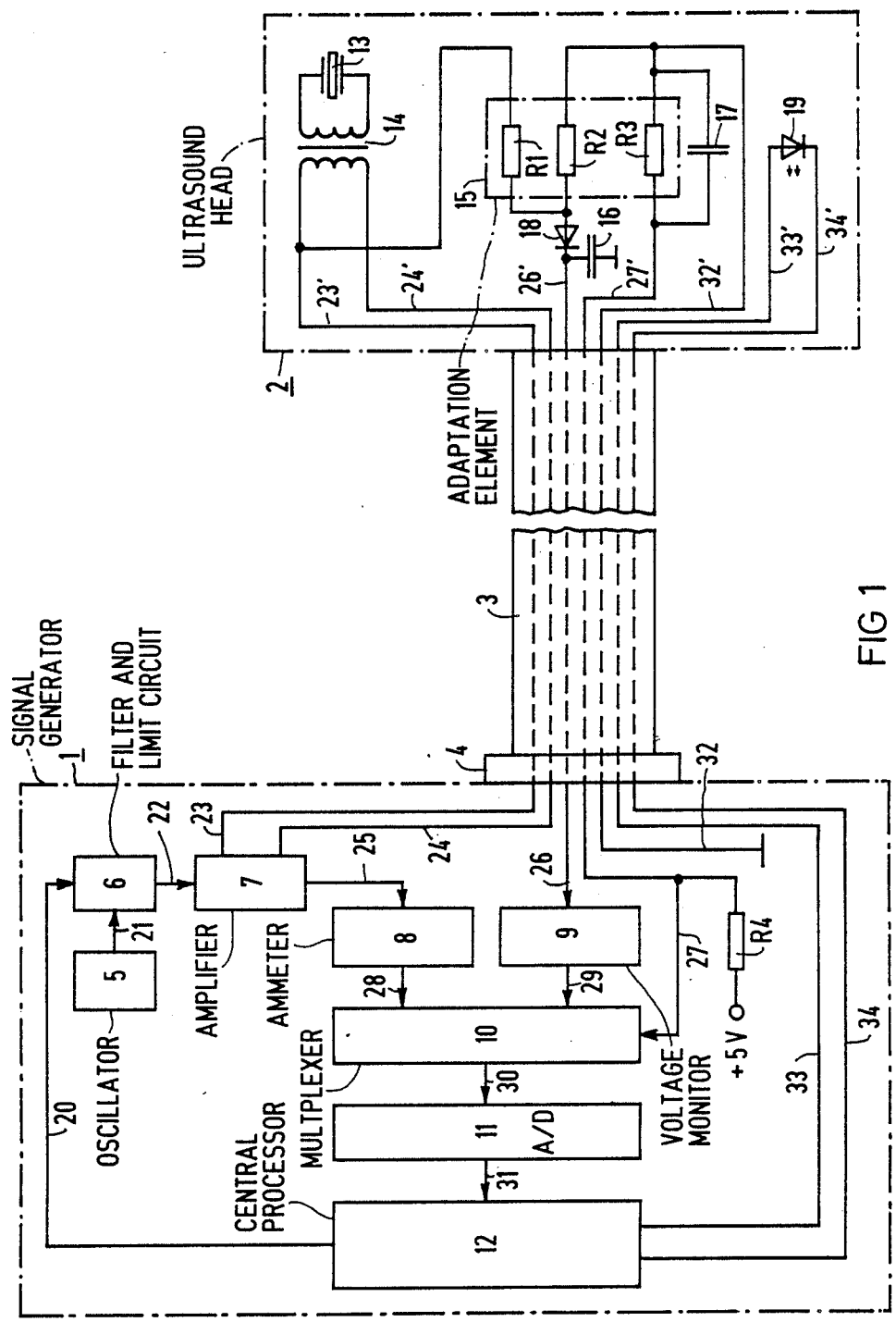
FIG. 1 is a schematic block diagram of a signal generator and an ultrasound head constructed in accordance with the principles of the present invention.

In the basic circuit diagram shown in FIG. 1, an electrical signal generator is generally referenced at 1, and an ultrasound head is generally referenced at 2. The ultrasound head 2 is coupled to the electrical signal generator 1 by a cable 3, inserted in a cable plug 4.

The electrical signal generator 1, among other components, includes an oscillator 5 (which, for example, supplies a signal at 875 kHz), a filter and limit circuit 6, and amplifier 7, an ammeter 8, a voltage monitor 9, a multiplexer 10, an analog-to-digital converter 11, and a central processor 12.

The ultrasound head 2 includes an ultrasound resonator 13 which is supplied with signals via a broadband transformer 14. The ultrasound head 2 also includes an adaptation element 15 formed of ohmic fixed resistors R1, R2 and R3. The adaptation element 15 is a portion of a matching circuit, which also includes at least the components 8 through 12 in the electrical signal generator 1.

The ultrasound head 2 also includes smoothing capacitors 16 and 17 and a rectifying diode 18. The signal generator 1 also includes a fixed ohmic resistor R4 connected to a voltage source of, for example, +5V.

The adaptation element 15 is in the form of an insertable IC base on which the ohmic fixed resistors R1, R2 and R3 are connected, such as by soldering. The adaptation element 15 is thus easily interchangeable on the circuit board contained in the ultrasound head 2, as described in further detail in connection with FIG. 2.

The ultrasound head 2 also includes a light emitting diode 19 as a display element, to indicate that the ultrasound head 2 is correctly coupled to the electrical signal generator 1 via the cable 3 and the cable plug 4 (i.e., to indicate that the ultrasound resonator is being driven according to the power which has been set).

The schematic representations for the signal generator 1 and the ultrasound head 2 show only those circuit components necessary for an understanding of the functioning of the present invention. Similarly, only the signal lines necessary to explain the operation of the basic components are shown in FIG. 1.

The oscillator 5 in the signal generator 1 generates high-frequency electrical signals which are supplied to the ultrasound resonator 13 of the ultrasound head 2 via the filter and limit circuit 6 and the amplifier 7, along signal lines 23 and 23', and 24 and 24', connected to the broadband transformer 14. The ultrasound resonator 13 converts the incoming electrical signals into ultrasound energy, and emits this energy, for example, into human body tissue for ultrasound therapy.

The ultrasound head 2 and the electrical signal generator 1 are matched to each other by the components 8 through 12 and the adaptation element 15 as long as no malfunctions are present in the operation of the ultrasound resonator 13. Such malfunctions may include, for example, mechanical rupture or depolarization due to overheating or electrolytic erosion of the treatment surface of the resonator carrier (shown in FIG. 2) in the case of ultrasound and stimulation current therapy. The adaptation element 15 is part of a control circuit for the drive of the ultrasound resonator 13, the remainder of the control circuit components being disposed in the signal generator 1. In a known manner, the divider voltage of the resistors R1 and R2 is conducted to the voltage monitor 9 via the rectifying diode 18 and the smoothing capacitor 16. This voltage is supplied to the voltage monitor 9 via lines 26' and 26. A correction signal (if needed) is acquired by the parallel circuit of the resistor R3 and the capacitor 17. This correction signal is conducted to the multiplexer 10 as well via lines 27 and 27'. The multiplexer 10 reads the supplied signals (from the ammeter 8 via line 28, the voltage monitor 9 via line 29, and via line 27) in cyclic fashion and supplies the result to the central processor 12 via the analog-to-digital converter 11. The central processor 12 undertakes a comparison of the incoming correction data, and generates a signal on line 20 which varies the transmission properties of the filter and limit circuit 6, or of the amplifier 7 in a known manner for achieving the desired matching of the ultrasound head 2 to the electrical signal generator 1.

If a malfunction occurs necessitating a replacement of the ultrasound resonator 13, new matching of the components of the signal generator 1 with the replacement resonator is required. In accordance with the principles of the present invention, such matching can be undertaken on site, for example at a clinic or in a physician's office. For this purpose, a service technician removes the old ultrasound resonator as well as the previous adapter element 15. A new matched pair is then substituted, i.e., a new ultrasound resonator 13 together with a new adapter element 15, matched thereto. The mating parts of each pair are already packaged in pairs by the manufacturer or distributor of the device, so that mistakes cannot occur during service. Dependent on the number of devices to be repaired, the service technician at the place of use simply needs a corresponding number of already-packaged pairs of mating ultrasound resonators 13 and adapter elements 15. Further equipment such as, for example, measuring and signal acquisition equipment, are therefore not required at the place of use for undertaking such an installation.

As described above, the adapter element 15 is easily interchangeable because it is in the form of an insertable (pluggable) IC base, the plugs being shown at 15a. The ultrasound resonator 13 is also easily replaceable, as shown in detail in FIG. 2.

Figure 2:
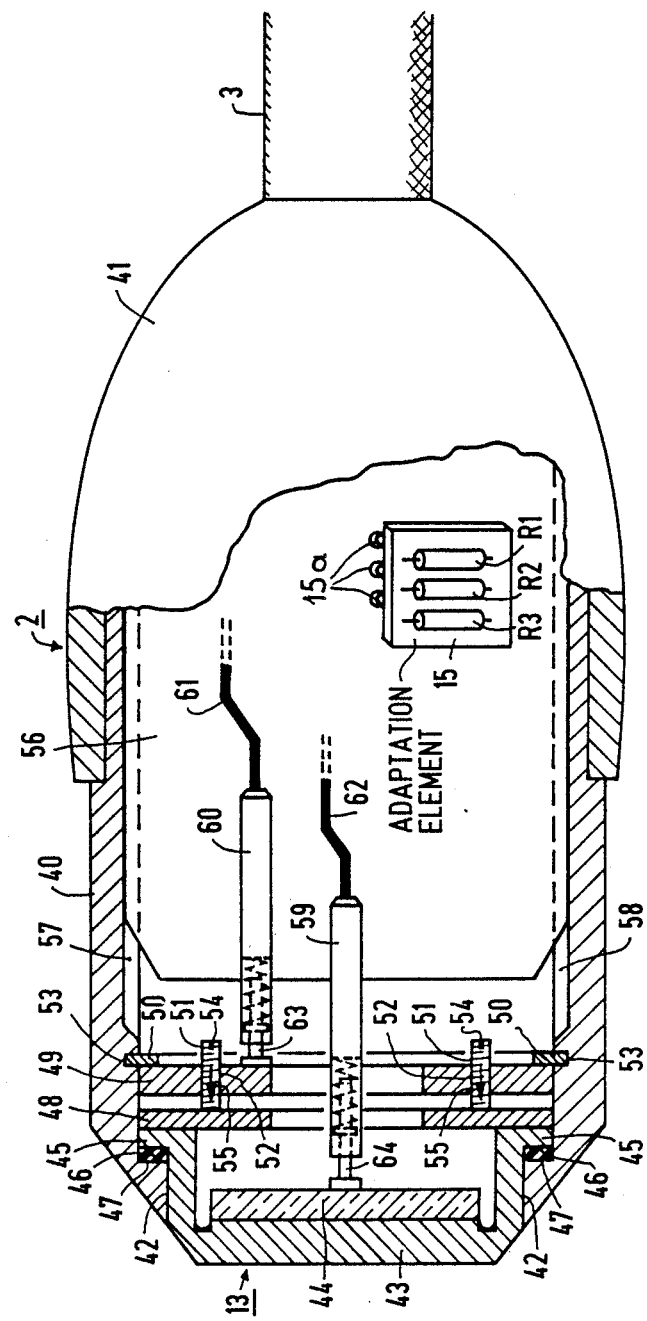
FIG. 2 is a side view of an ultrasound head constructed in accordance with the principles of the present invention, shown partly in section.

An exemplary embodiment of an ultrasound head constructed in accordance with the principles of the present invention is shown in FIG. 2. The ultrasound head 2 includes a proximal housing section 40 consisting of, for example, plastic, and a distal housing section 41, consisting also, for example, of plastic. The housing sections 40 and 41 engage in a press fit. In FIG. 2, the proximal housing section 40 is shown in longitudinal section, and the distal housing section 41 is shown partly broken away.

The proximal housing section 40 has an opening 42 at the application side thereof, at which an ultrasound resonator 13 is disposed. The ultrasound resonator 13 includes a resonator carrier 43 (consisting, for example, of aluminum) and a ceramic resonator disc 44 attached to the interior of the carrier 43 by suitable adhesive. The resonator carrier 43 has an outwardly crimped edge 45 seated on an inside shoulder 47 of the proximal housing section 40, with an intervening sealing ring 46. A pressing mechanism is provided for maintaining the carrier in place. This mechanism includes a thin, perforated metal disc 48 (consisting, for example, of steel) a thick, perforated metal disc 49 (also consisting, for example, of steel), a circular clip 50, and a number (for example, 3) of metallic clamping screws 51. Each screw 51 is disposed in an associated threaded bore 52 of the metal disc 49, and is adjustable perpendicularly relative to the metal disc 49 so as to press the resonator carrier 43 against the sealing ring 46, and the shoulder 47.

During assembly, the sealing ring 46 is first placed on the inside shoulder 47 of the proximal housing section 40. Subsequently, the resonator carrier 43 and the ceramic resonator disc 44 are inserted into the opening 42, and arranged as shown in FIG. 2 relative to the shoulder 47 and the sealing ring 46. The thin metal disc 48 and the thick metal disc 49 are then inserted, and the circular clip 50 is inserted into an annular groove 53 in the inside wall of the proximal housing section 40. Each clamping screw 51 has a slot 54 for receiving the blade of a screwdriver. By turning with the screwdriver, the clamping screws 51 move in the direction of the arrow 55. The circular clip 50 serves as an abutment for the thick metal disc 49, and thus the total number of clamping screws 51 press the ultrasound resonator 13 into the opening 42 in a sealed fashion via the thin metal disc 48.

The distal housing section 41, to which one end of the cable 3 is attached, contains a printed circuit board 56 on which the electrical components for the circuitry of the ultrasound head 2 are mounted, the circuit board 56 being the so-called "mother board". These components include the adapter element 15, in the form of an IC base with the ohmic resistors Rl, R2 and R3 thereon. The adaptation element 15 may be plugged into an IC socket on the printed circuit board 56, or may be directly soldered thereto. When the distal housing section 41 is engaged with the proximal housing section 40, the printed circuit board 56 is held by interior longitudinal grooves 57 and 58 of the proximal housing section 40.

Spring contact pins 59 and 60 are also shown in FIG. 2 for making electrical and mechanical contact with the ultrasound resonator 13. The respective electrical leads of the spring contact pins 59 and 60 are soldered to the circuit board 56, and are thus in electrical contact with conductor runs 61 and 62 leading to a voltage supply (not shown). The pins 59 and 60 have respective contact feet 63 and 64. The foot 64 of the pin 59 is in mechanical and electrical contact with the ceramic resonator disc 44. The foot 63 of the pin 60 is in mechanical and electrical contact with the resonator carrier 43 via the thick metal disc 49, the clamping screws 51, and the thin metal disc 48.

In the event of a malfunction, the malfunctioning ultrasound resonator 13 (the resonator carrier 43 together with the ceramic resonator disc 44) is dismantled in the reverse of the sequence described above, and can be easily replaced by a new, properly functioning ultrasound resonator 13, at the same time a new adaptation element 15 is inserted in the circuit board 56 for matching the new resonator to the components of the signal generator 1.

Although modifications and changes may be suggested by those skilled in the art it is the intention of the inventors to embody within the patent warranted hereon all changes and modifications as reasonably and properly come within the scope of their contribution to the art.

We claim as our invention:

1. An ultrasound device comprising: an ultrasound head; an ultrasound transducer;
    an adaptation element electrically connected to said ultrasound transducer and means for removably mounting said ultrasound transducer and said adaptation element in said ultrasound head;
    electronic means electrically connected to said ultrasound transducer in a signal path which includes said adaptation element for generating electronic signals for driving said ultrasound transducer;
    said adaptation element including a plurality of electrical components having pre-set values for electrically matching said ultrasound transducer to said electronic means and wherein said means for removably mounting enables substitution of a new ultrasound transducer and a new adaptation element matched thereto whereby said new ultrasound transducer is electrically matched to said electronic means without further adjustment.

2. An ultrasound device as claimed in claim 1, wherein said components of said adaptation element comprise a plurality of ohmic fixed resistors mounted on an IC base.

3. An ultrasound device as claimed in claim 1, wherein said electronic means comprises:
    means for supplying current to said ultrasound transducer;
    an ammeter which measures said current supplied to said ultrasound transducer;
    voltage monitoring means for monitoring the voltage supplied to said ultrasound transducer;
    a multiplexer to which output from said ammeter and said voltage monitor are supplied;
    an analog-to digital converter having an input connected to an output of said multiplexer to which signals from said ammeter and said voltage monitoring means are alternatingly supplied by said multiplexer; and
    processor means having an input connected to an output of said analog-to-digital converter for controlling said means for generating electronic signals by comparing said signals from said ammeter and said voltage monitoring means to reference values and altering the operations of said means for generating electronic signals based on the amount of deviation of said signals from said ammeter and said voltage monitoring means from said reference values.

4. An ultrasound device as claimed in claim 1, wherein said values of said components of an adaptation element are uniquely matched to an ultrasound transducer so that said ultrasound transducer and said adaptation element form a unique pair adapted for use and replacement together.

5. An ultrasound device as claimed in claim 1, wherein said ultrasound head includes a printed mother board, and wherein said adaptation element is plugged into receptacles in said printed mother board.

6. A method for substituting components in an ultrasound device having an ultrasound head which includes an ultrasound transducer and having a drive circuit for driving said ultrasound transducer,
    wherein said ultrasound transducer is removably mounted in said ultrasound head and an
    adaptation element which is electrically connected in a signal path between said ultrasound transducer is removably mounted in said ultrasound head, said method comprising the steps of:
    electrically matching said adaptation element to said ultrasound transducer before installation of said adaptation element and said ultrasound transducer in said ultrasound head;
    installing the matched ultrasound transducer and adaptation element as a pair in said ultrasound head; and
    removing the matched ultrasound transducer and adaptation element as a pair from said ultrasound head in the event of a substitution of said ultrasound transducer.

* * * * *